April 13, 1971 R. V. LINDQUIST Plant Pat. 3,044
ROSE PLANT
Filed June 17, 1969
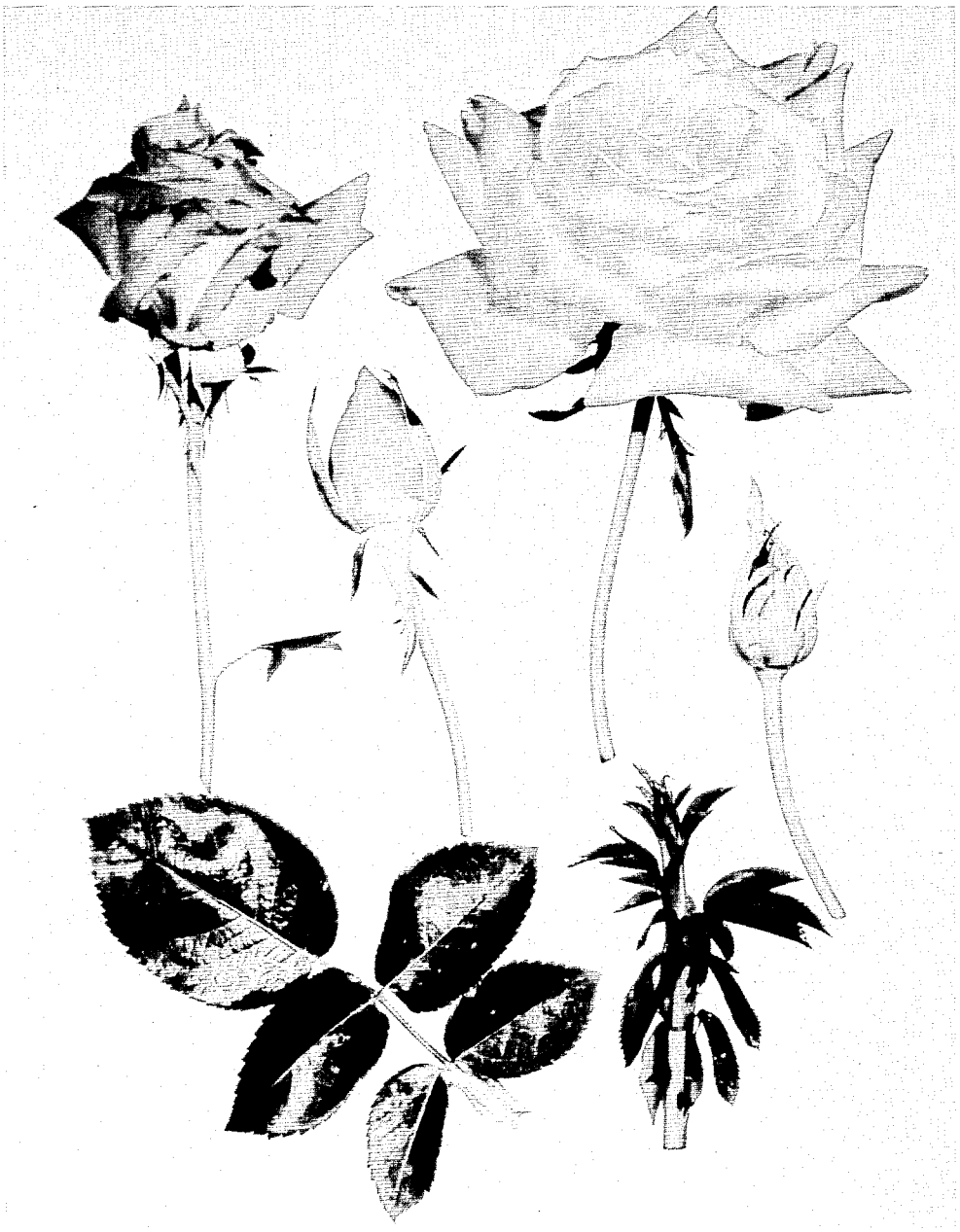
Inventor.
Robert V. Lindquist
By: Robb & Robb
Attorneys.

United States Patent Office

Plant Pat. 3,044
Patented Apr. 13, 1971

3,044
ROSE PLANT

Robert V. Lindqust, Riverside, Calif., assignor to Hemet Wholesale, Hemet, Calif.

Filed June 17, 1969, Ser. No. 834,180
Int. Cl. A01h 5/00
U.S. Cl. Plt.—11 1 Claim The present invention relates to a new and distinct variety of rose plant of the hybrid tea class, which was originated by me by crossing the rose variety known as "Kordes' Perfecta" (Plant Patent No. 1,604) with the rose variety known as "Granada" (Plant Patent No. 2,214), the former being the seed parent, and the latter being the pollen parent.

As the result of this breeding, I have produced a new rose variety of exhibition quality which is particularly characterized as to novelty by the unique combination of the following features which are outstanding therein and which distinguish it from its parents, as well as from all other rose varieties of which I am aware:

(1) A vigorous and bushy plant habit;
(2) Attractive bright Irish green foliage which covers the plant well;
(3) Perfectly formed flower buds which open slowly to attractive blooms usually borne singly and having symmetrically shaped petals forming large, classic flowers which retain their classic form even when fully open;
(4) A distinctive and attractive soft medium pink flower color; and
(5) A pleasing fruity flower fragrance.

Asexual reproduction of my new variety by budding, as performed at Hemet, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new rose variety, with color terminology in accordance with the Royal Horticultural Colour Chart, published by the Royal Horticultural Society of London:

Type: Hardy; bush; greenhouse; seedling; for cut flowers and for garden decoration.
Class: Hybrid tea.
Breeding: Seedling.
*Seed parent.*—"Kordes' Perfecta."
*Pollen parent.*—"Granada."
Propagation: Holds its distinguishing characteristics through succeeding propagations by budding.

*Flower*

Locality where grown and observed: Hemet, Calif.
Flowers borne: Usually singly, but sometimes 2 or 3 to stem; on medium length to long stems of normal strength.
Quantity of bloom: Free, both outdoors and in greenhouse.
Continuity: Continous during growing season.
Fragrance: Fruity tea.
Bud:
*Peduncle.*—From average length to long; average caliper; bending; moderately smooth; few gland-tipped cilia; few prickles. Color—Yellow-Green, Group 146 B.
*Before calyx breaks.*— Size—medium. Form—medium length; ovoid; with a conspicuous neck; with foliaceous appendages and few gland-tipped cilia on the surface of the bud; usually with bristle-like foliaceous parts extending beyond the tip of the bud equal to ¼ of its length.
*As calyx breaks.*—Color—near Red-Purple, Group 59 A.
*Sepals.*—Inner surface—with fine, wooly tomentum; lined with gland-tipped cilia and hairs. Margins—some sepals have foliaceous appendages.
*As first pela opens.*—Size—Average. Form—medium length; from pointed to ovoid. Color—Outside—near Red-Purple, Group 63 B, with small base of near Yellow, Group 13 A. Inside—near Red-Purple, Group 63 A, with small base of near Yellow, Group 13 A.
*Opening.*—Opens up well; is not prevented from opening by hot, wet or dry weather.

Bloom: Size (when fully open)—large; from 5 inches to 6 inches.
*Petalage.*—Double; from 35 to 45 petals, plus 6 to 8 petaloids; arranged irregularly.
*Form.*—High-centered at first, but becoming high-centered globular; petals being at first somewhat tightly cupped, with tips reflexed outward, but later becoming somewhat loosely cupped, with tips reflexed outward, at maturity.
Petals:
*Texture.*—Medium thickness.
*Appearance.*—Inside—slightly shiny. Outside—slightly shiny.
*Shape.*—Outside—oval. Intermediate—oval, but some with small pointed apex, and some with apex rounded to flat. Inside—nearly oval; most with apex rounded, but some petals have pointed apex.

This description of a newly opened flower was made from a rose grown outdoors during the month of May at Hemet, Calif.:
*Color.*—*Outer petal*—outside surface: near Red-Purple, Group 63 B, with base of near Yellow-Orange, Group 15 C; inside surface: near Red-Purple, Group 63 A, shading to near Red-Purple, Group 63 B, and with base of near Yellow-Orange, Group 15 A.
*Intermediate petal*—outside surface: near Red, Group 52 C, shading to near Red, Group 41 C, with base of near Yellow-Orange, Group 15 B; inside surface: near Red, Group 52 C, shading to near Red, Group 41 C, and with base of near Yellow-Orange, Group 15 A; *Inner petal*—outside surface: near Red, Group 52 C, with base of near Yellow-Orange, Group 15 B; inside surface: near Red, Group 52 B, shading to near Red, Group 41 C, and with base of near Yellow-Orange, Group 15 A.

This description was made from a rose that was open for three days outdoors during the month of May, at Hemet, Calif.:
*Color.*—*Outer petal*—Outside surface; near Red-Purple, Group 61 C, shading to near Red-Purple, Group, 62 A, and with base of near Yellow-Orange, Group 15 C; inside surface: near Red-Purple, Group 63 A, shading to near Red-Purple, Group 61 D, and with base of near Yellow-Orange, Group 15 D.
*Inner petal*—outside surface: near Red-Purple, Group 62 A, shading to near Red, Group 41 D, and with base of near Yellow-Orange, Group 15 A; inside surface: near Red, Group 63 B, shading to near Red, Group 41 C, and with base of near Yellow-Orange, Group 15 A.

*General color effect.*—Newly opened flower—Pink blend. 3-days open—Pink blend.

*Behavior.*—Drop off cleanly.

*Flower longevity.*—On bush in garden—4 or 5 days in May. Cut roses grown outdoors and kept at living-room temperatures—3 or 4 days in May. Cut roses grown in greenhouse and kept at living-room temperatures—3 or 4 days in May.

*Reproductive organs*

Stamens: Average number; arranged regularly about pistils.

Filaments: From medium length to long; most with anthers.

Anthers: Medium size; all open approximately at once. Color—upper side—near Yellow-Orange, Group 22 A. Under side—near Yellow-Orange, Group 22 A.

Pollen: Somewhat sparse. Color—near Yellow-Orange—Group 20 B.

Pistils: Average number (approximately 150).

Styles: Uneven; average length; average caliper; somewhat bunched.

Stigma: Color—near Yellow-Orange, Group 20 A.

Ovaries: Usually most enclosed in calyx.

Hips: Average length; globular; moderately smooth; walls thick and fleshy. Color—near Yellow-Orange, Group 22 A.

Sepals: Falling soon; medium length; spear-shaped; recurved. Color—inside:—near Yellow-Green, Group 148 C; outside:—near Green, Group 143 C.

Seeds: Average number (from 25 to 30); from medium size to large.

*Plant*

Foliage:

*Leaves.*—Compound of 3–5 leaflets; normal abundance; from medium size to large; moderately heavy; very glossy.

*Leaflets.*—Shape—oval; apex—mucronate; base—round; margin—irregularly serrate.

*Color.*—Mature—upper surface: near yellow-Green, Group 147 A; under surface: near Yellow-Green, Group 148 B. Young—upper surface: near Yellow-Green, Group 147 A; under surface; near Yellow-Green, Group 147 B.

*Rachis (the supporting stem of the compound leaf).*—Average size. upper side—grooved; some stipitate glands on edges; under side—moderately smooth; with stipitate glands.

*Stipules.*—From medium length to long; medium width; with medium length points turning out at an angle of more than 45°.

*Disease resistance.*—Better than average resistance to mildew, as determined by comparison with other rose varieties grown under comparable conditions at Hemet, Calif.

Growth:

*Habit.*—Upright; much-branched.

*Growth.*—Very free; vigorous.

*Canes.*—From medium caliper to heavy.

*Main stems.*—*Color*—near Yellow-Green, Group 146 B.

*Large prickles*—few; from medium length to long; almost straight; with medium length, narrow base. Color—near Greyed-Orange, Group 165 A.

*Small prickles*—few. Color—near Greyed-Orange, Group 165 A.

*Hairs*—none.

*Branches.*—*Color*—near Yellow-Green, Group 146 C.

*Large prickles*—few; from medium length to long; almost straight; with medium length, narrow base. Color—near Greyed-Orange, Group 165 A.

*Small prickles*—few. Color—near Greyed-Orange, Group 177 B.

*Hairs*—none.

*New shoots.*—*Color*—near Red-Purple, Group 59 A.

*Large prickles*—few; medium length; almost straight; with medium length, moderately narrow base. Color—near Red-Purple, Group 59 B.

*Small prickles*—few.

*Hairs*—none.

I claim:

1. A new and distinct variety of rose plant of the hybrid tea class, substantially as herein shown and described, characterized particularly as to novelty by the unique combination of a vigorous and bushy plant habit, attractive bright Irish green foliage which covers the plant well, perfectly formed flower buds which open slowly to attractive blooms usually borne singly and having symmetrically shaped petals forming large, classic flowers which retain their classic form even when fully open, a distinctive and attractive soft medium pink flower color, and a pleasing fruity flower fragrance.

No references cited.

ROBERT BAGWILL, Primary Examiner